United States Patent
Gerder

(10) Patent No.: US 7,489,808 B2
(45) Date of Patent: Feb. 10, 2009

(54) PROCESS AND DEVICE FOR ACTIVATING A MEDICAL INSTRUMENT

(75) Inventor: Henning Gerder, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 953 days.

(21) Appl. No.: 10/969,820

(22) Filed: Oct. 21, 2004

(65) Prior Publication Data

US 2005/0180615 A1 Aug. 18, 2005

(30) Foreign Application Priority Data

Feb. 12, 2004 (DE) .............. 10 2004 006 842

(51) Int. Cl.
*G06K 9/00* (2006.01)
*G05B 19/00* (2006.01)

(52) U.S. Cl. ............... 382/124; 382/128; 340/5.82

(58) Field of Classification Search .......... 382/115, 382/116, 124, 128, 209, 218; 340/5.52, 5.53, 340/5.8, 5.82, 5.83; 607/31; 902/3; 283/68; 713/186

See application file for complete search history.

(56) References Cited

U.S. PATENT DOCUMENTS

| | | | | |
|---|---|---|---|---|
| 6,927,671 B2 * | 8/2005 | DeBono | .............. | 340/5.83 |
| 6,948,492 B2 * | 9/2005 | Wermeling et al. | .... | 128/200.14 |
| 6,961,448 B2 * | 11/2005 | Nichols et al. | .............. | 382/115 |
| 6,963,659 B2 * | 11/2005 | Tumey et al. | .............. | 382/116 |
| 2002/0038392 A1 | 3/2002 | De La Huerga | | |
| 2003/0140928 A1 | 7/2003 | Bui et al. | | |
| 2003/0140929 A1 | 7/2003 | Wilkes et al. | | |
| 2004/0010425 A1 * | 1/2004 | Wilkes et al. | .............. | 705/3 |

FOREIGN PATENT DOCUMENTS

| | | |
|---|---|---|
| DE | 197 47 353 | 4/1999 |
| DE | 198 09 952 A1 | 9/1999 |
| DE | 201 04 810 | 9/2001 |
| DE | 101 16 650 A1 | 11/2002 |
| EP | 0 980 688 | 2/2000 |
| WO | WO 99/10029 | 3/1999 |
| WO | WO 01/04824 | 1/2001 |
| WO | WO 2004/107277 | 12/2004 |

* cited by examiner

*Primary Examiner*—Daniel G Mariam
(74) *Attorney, Agent, or Firm*—McGlew and Tuttle, P.C.

(57) ABSTRACT

A simple and reliable process for activating a medical instrument, for example, one containing an anesthetic agent- or drug-dispensing unit (23) as well as a respirator drive (24) for respirating a patient is provided. The medical instrument is switched on, and a sensor (20) for detecting biometric features of a user, which is connected to or communicates with the medical instrument, is activated by the switching on, so that the individual biometric features of a certain user are detected. Te detected individual biometric features of the certain user are compared with the biometric features of at least one user within a preset time period. The medical instrument is released for the operation by the certain user only in case of agreement between the detected individual biometric features of the certain user and biometric features of at least one user, which were entered in the memory in advance.

15 Claims, 2 Drawing Sheets

PROCESS AND DEVICE FOR ACTIVATING A MEDICAL INSTRUMENT

CROSS REFERENCE TO RELATED APPLICATIONS

This application claims the benefit of priority under 35 U.S.C. § 119 of German application 10 2004 006 842.9 filed Feb. 12, 2004, the entire contents of which are incorporated herein by reference.

FIELD OF THE INVENTION

The present invention pertains to a process for activating a medical instrument and to a corresponding device.

BACKGROUND OF THE INVENTION

Processes for configuring monitors associated with medical instruments as well as for releasing modes of operation at a medical instrument have become known from the German preliminary published patent applications DE 198 09 952 A1 and DE 101 16 650 A1, wherein the configuration data and the modes of operation are read from an external electronic, optical or magnetic storage medium into the respective medical instrument.

SUMMARY OF THE INVENTION

The object of the present invention is to provide a simple and reliable process for activating a medical instrument by a user without the use of an external storage medium by the user.

According to the invention, a process is provided for activating a medical instrument. The medical instrument is switched on. A sensor means, for detecting biometric features of a user, which is connected to or communicates with the medical instrument, is activated by the switching on of the medical instrument, so that the individual biometric features of a certain user are detected. The detected individual biometric features of the certain user are compared within a preset time period with the biometric features of at least one user, which were entered in the memory in advance, so that the medical instrument is released for the operation by the certain person only in case of agreement between the detected individual biometric features of the certain user and the biometric features of at least one user, which were entered in the memory in advance.

According to another aspect of the invention, a device is provided for activating a medical instrument with an anesthetic agent-dispensing or drug-dispensing unit. The device has a central control and evaluating unit. A sensor means is provided for detecting biometric features of a user. The device has an output and monitoring unit. Depending on the individual biometric features of a certain user, which were detected by means of the sensor means, and after comparison with biometric features of at least one user, which were entered in the memory in advance, the said control and evaluating unit releases the medical instrument.

An important advantage of the process and device according to the present invention is obtained by the release of the medical instrument (an unlocking or an enablement to function) when the individual biometric features of a certain user, which are detected by means of a sensor means, agree with the biometric features of at least one user, which were entered in the memory in advance. The biometric features preferably consist of person-specific measured values of fingerprints (so-called "fingerprints"), iris or iris patterns or elements of human speech. The features are detected with prior-art suitable sensor means such as optical or thermal detection systems for fingerprints or eye features, or microphones for speech signals, and linked with corresponding hardware and software for signal processing, for forming a reference, and for classification. The signal processing is usually performed in a central control and evaluating unit of the medical instrument. The sensor means of the medical instrument communicates with the control and evaluation unit of the device via communication interfaces.

After the medical instrument, especially an anesthesia apparatus or respirator, has been switched on, the medical instrument preferably activates the associated sensor means; which is especially integrated in the instrument, for detecting biometric features of a user, so that, e.g., an individual fingerprint is detected. The detected individual biometric features of the certain user are then compared with the biometric features of at least one user, which were entered in the memory in advance, within a time period preset for the detection, which is, e.g., a few minutes, so that the medical instrument is released for the operation by the certain user only in case of agreement of the detected individual biometric features of the certain user with the biometric features being stored.

The individual stored biometric features of a certain user are preferably stored and preferably linked with associated personal, patient- and/or device-specific data, so that, e.g., user-specific operator or screen display options are available after the activation of the device.

With the process of the invention, after the release of the medical instrument, the certain user may select a learning program offered by the device, so that the individual biometric features of a certain additional user are detected by means of the sensor means and entered in the memory. The individual biometric features of a certain user may be stored with associated personal, patient- and/or instrument-specific data. The instrument-specific data may comprise operating and screen options of the medical instrument.

With the process of the invention, the biometric features may comprise measured values of fingerprints, iris or iris patterns or elements of human speech or other measurable characteristics particular to an indivisual.

For the detection of a fingerprint, the device may employ a sensor means designed for the thermal detection of a fingerprint.

The device of the invention may provide the medical instrument as a drug-dispensing unit. This drug dispensing unit may be connected with a respirator drive for respirating a patient. The respirator drive may advantageously include a radial flow compressor. The anesthetic agent-dispensing or drug-dispensing unit may form a combined anesthesia workstation with the respirator drive.

The mode of operation of the process according to the present invention and of the corresponding device will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 2:
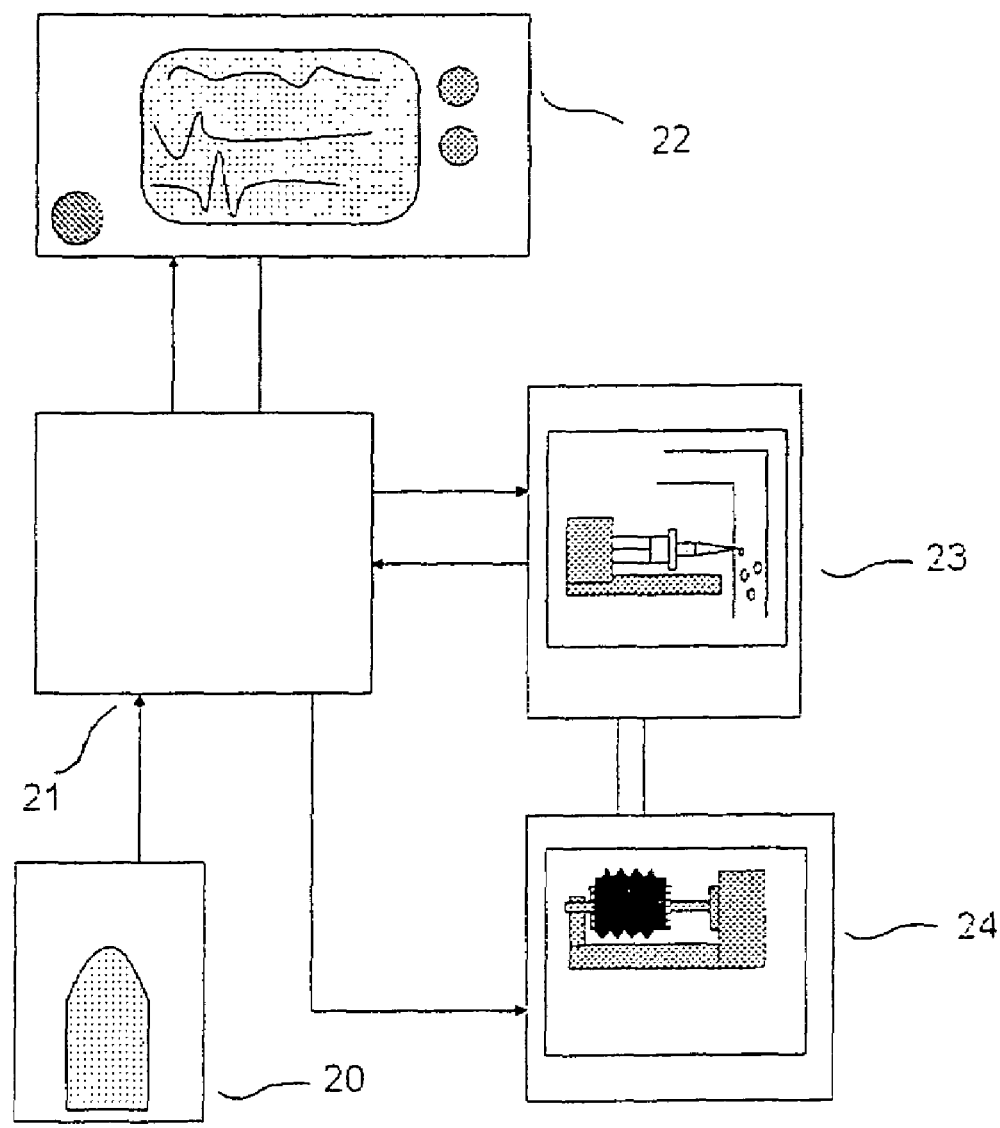
FIG. 2 is a schematic view showing an arrangement of a device for activating a medical instrument.

The arrangement according to FIG. 2 pertains to a medical instrument with an anesthetic agent or drug dispensing unit 23, which is connected with a respirator drive 24, for example, in the form of a pump, for respirating a patient. The elements 23, 24 are controlled via a central control and evaluating unit 21. A sensor means 20 is provided for detecting biometric features of a user. The sensor means 20 is, for example, a thermal detector means for a fingerprint and is connected to the control and evaluating unit 21.

The output and monitoring unit 22 is used to switch the entire arrangement on and off, to operate same and to display the entire arrangement, preferably also for generating the acoustic and/or optical alarm display for preset operating states.

Figure 1:
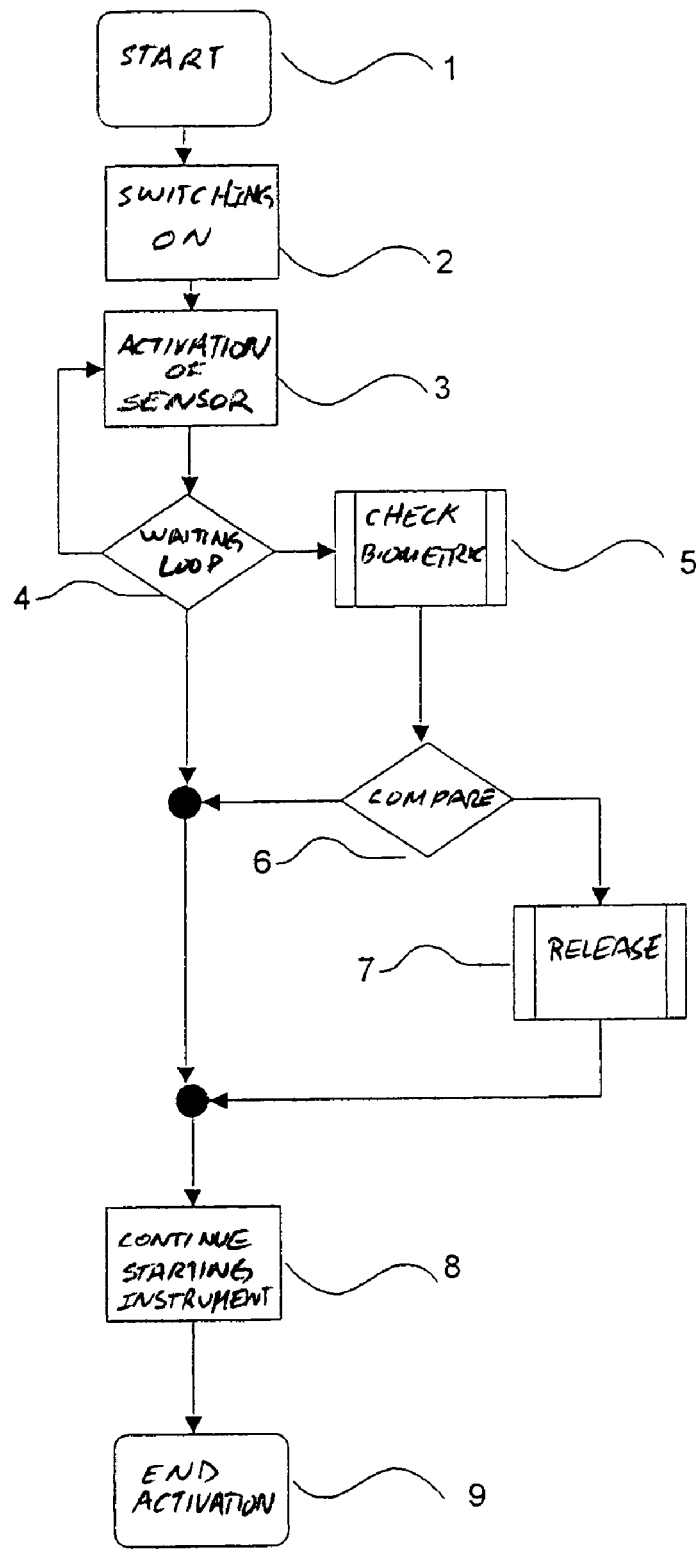
FIG. 1 is a schematic flow chart of the process for activating a medical instrument.

The process for activating a medical instrument according to FIG. 1 is explained in FIG. 2 by means of an exemplary embodiment.

The start 1 of the activation begins with the switching on 2 of the instrument with an automatic self-test of the instrument. This is followed by the activation at 3 of the sensor means 20 for detecting biometric features of a user. The polling of the sensor means 20 takes place in a waiting loop 4, which comprises, for example, a time period of a few minutes. The detected individual biometric features of a certain user are then checked in 5 for completeness and legibility and compared in 6 with biometric features of at least one user, which were entered in a memory of control and evaluating unit 21 in advance. In case of agreement between the detected individual biometric features of the certain user with the biometric features of at least one user, which were entered in the memory in advance, the medical instrument is released according to 7, and special program routines are loaded, so that the starting of the instrument is continued in 8 and the activation ends in 9.

Various special branchings, of which the following will be explicitly mentioned here, are possible during the process described:

During or after the polling of the sensor means 20, there is an automatic branching into an instrument menu, in which the certain user can select certain operating or screen options.

If an additional user is unknown to the instrument, the additional user with his individual biometric features can be read in during a preset time period in a learning program.

During the running operation of the instrument, either a special setting menu or a special handling combination by means of, e.g., a rotary knob and a sensor means 20 is used to poll a profile menu in order to generate and store individual application-specific profiles.

After the activation of the medical instrument, a special application of the process releases the dispensing of special drugs, for example, in an intensive care unit. The certain user places the infusion cassette into an infusion pump, the infusion pump recognizes the drug by means of an electronic marking, and classifies the drug to a certain risk level after comparison with a networked data bank. The user selects a certain dosage. The user must release the dosage by means of the sensor means 20. Any further change in the set point of the dosage must be confirmed via the sensor means 20.

This expanded application prevents abuse and can be used to retrace what was done to the patient and by whom within the framework of a quality management system.

While specific embodiments of the invention have been shown and described in detail to illustrate the application of the principles of the invention, it will be understood that the invention may be embodied otherwise without departing from such principles.

What is claimed is:

1. A process for activating a medical instrument, the process comprising the steps of:
   switching the medical instrument on and activating a sensor means for detecting biometric features of a user, the sensor means being connected to or communicating with the medical instrument so that the individual biometric features of a certain user are detected;
   comparing the detected individual biometric features of the certain user within a preset time period with the biometric features of at least one user, which were entered in a memory in advance;
   releasing the medical instrument for operation by the certain person only in case of agreement between the detected individual biometric features of the certain user and the biometric features of the at least one user, which were entered in the memory in advance, wherein the individual biometric features of a certain user are stored with associated personal, patient- and/or instrument-specific data said instrument-specific data comprising operating and screen options of the medical instrument.

2. A process in accordance with claim 1, wherein after the release of the medical instrument, the certain user selects a learning program associated with said medical instrument, so that the individual biometric features of a certain additional user are detected by means of the sensor means and entered in the memory.

3. A process in accordance with claim 1, wherein the biometric features comprise measured values of one or more of fingerprints, iris or iris patterns or elements of human speech.

4. A process in accordance with claim 1, wherein said medical instrument is a anesthetic-dispensing or drug-dispensing unit.

5. A process in accordance with claim 4, further comprising the step of:
   controlling an amount of an anesthetic or a drug delivered from said anesthetic agent-dispensing or drug-dispensing unit to the patient via said control and evaluating unit after said anesthetic agent-dispensing or drug-dispensing unit is released via said sensor means.

6. A device for activating a medical instrument, the device comprising:
   an anesthetic agent-dispensing or drug-dispensing unit;
   a central control and evaluating unit with an associated memory, said memory comprising user biometric data;
   a sensor means for detecting biometric features of a user and for releasing an anesthetic or a drug via said anesthetic agent-dispensing or drug-dispensing unit to a patient; and
   an output and monitoring unit, said control and evaluating unit being programmed such that said control and evaluating unit compares said biometric features of the user from said sensor means with said user biometric data, said control and evaluating unit controlling said anesthetic agent-dispensing or drug-dispensing unit such that a flow of an anesthetic or a drug is delivered to a patient via said anesthetic agent-dispensing or drug-dispensing unit when said biometric features of the user corresponds to said user biometric data, said control and evaluating unit saving said flow of said anesthetic or said drug as patient treatment data in said memory.

7. A device in accordance with claim 6, wherein said sensor means comprises a device for the thermal detection of a fingerprint.

8. A device in accordance with claim 6, further comprising a respirator drive for respirating a patient, wherein the drug-dispensing unit is connected with said respirator drive for respirating a patient.

9. A device in accordance with claim 8, wherein the respirator drive has a radial flow compressor.

10. A device in accordance with claim 8, wherein the anesthetic agent-dispensing or drug-dispensing unit forms a combined anesthesia workstation with the respirator drive.

11. A process for activating a medical instrument, the process comprising the steps of:
   providing an anesthetic agent-dispensing or drug-dispensing unit;
   providing a central control and evaluating unit with an associated memory, said memory comprising user biometric data, said user biometric data being programmed in said memory in advance;
   providing a sensor means for detecting biometric features of a user and for releasing an anesthetic or a drug to a patient, the sensor means being connected to or communicating with the anesthetic agent-dispensing or drug-dispensing unit;
   providing an output and monitoring unit for on and off switching;
   switching the anesthetic agent-dispensing or drug-dispensing unit on and activating the sensor means to detect biometric features of a user;
   comparing the detected individual biometric features of the user within a preset time period with said user biometric data;
   releasing the anesthetic agent-dispensing or drug-dispensing unit for operation via said sensor means when the detected individual biometric features of the user corresponds to said user biometric data;
   controlling an amount of an anesthetic or a drug delivered from said anesthetic agent-dispensing or drug-dispensing unit to the patient via said control and evaluating unit after said anesthetic agent-dispensing or drug-dispensing unit is released;
   saving said amount of said anesthetic or said drug to said memory as patient dosage data.

12. A process in accordance with claim 11, wherein after the release of the medical instrument, the user selects a learning program associated with said anesthetic-dispensing or drug-dispensing unit, so that the individual biometric features of a certain additional user are detected by means of the sensor means and entered in the memory.

13. A process in accordance with claim 11, wherein the individual biometric features of the user are stored with associated personal, patient- and/or instrument-specific data.

14. A process in accordance with claim 13, wherein the instrument-specific data comprise operating and screen options of the medical instrument.

15. A process in accordance with claim 11, wherein the biometric features comprise measured values of one or more of fingerprints, iris or iris patterns or elements of human speech.

* * * * *